United States Patent [19]
Procházka et al.

[11] 3,980,631
[45] Sept. 14, 1976

[54] NOVEL ANALOGS OF DEAMINO-VASOPRESSIN WITH A MODIFIED DISULFIDE BRIDGE AND MANUFACTURING PROCESS THEREOF

[75] Inventors: Zdenko Procházka, Upice; Tomislav Barth, Roztoky; Jošeph Henry Cort, Prague; Karel Jost, Prague; Frantisek Sorm, Prague, all of Czechoslovakia

[73] Assignee: Ceskoslovenska akademie ved, Prague, Czechoslovakia

[22] Filed: Oct. 7, 1974

[21] Appl. No.: 512,429

[30] Foreign Application Priority Data
Nov. 9, 1973 Czechoslovakia ................ 7700-73

[52] U.S. Cl. ........................... 260/112.5 R; 424/177
[51] Int. Cl.$^2$ ................. C07C 103/52; A61K 37/00
[58] Field of Search ............................... 260/112.5

[56] References Cited
OTHER PUBLICATIONS
Hase et al., J. Am. Chem. Soc. 94, 3590–3600 (1972).
Jost et al., Coll. Czech. Chem. Comm., 32, 1229–1241 (1967).
Jost et al., Coll. Czech. Chem. Comm., 36, 234–245 (1971).
Prochazka et al., Coll. Czech. Chem. Comm., 37, 289–298 (1972).
Jost et al., Coll. Czech. Chem. Comm., 36, 2795–2808 (1971).

*Primary Examiner*—Lewis Gotts
*Assistant Examiner*—Reginald J. Suyat
*Attorney, Agent, or Firm*—Murray Schaffer

[57] ABSTRACT

Stepwise synthesis in solution and cyclization by means of active esters or another method suitable for peptide bond formation were used to prepare analogues of deamino-vasopressin with the disulphide bridge altered to the thioether group. In sequence position 8 of the peptide chain the analogs differed by the nature of basic amino acid. Typical vasopressin-like activities, mainly antidiuretic, were very high in these analogs; of particular importance will be their haemodynamic activity.

3 Claims, No Drawings

NOVEL ANALOGS OF DEAMINO-VASOPRESSIN WITH A MODIFIED DISULFIDE BRIDGE AND MANUFACTURING PROCESS THEREOF

The invention relates to novel analogs of deaminovasopressin with a modified disulfide bridge and manufacturing process thereof.

Vasopressin, the posterior pituitary gland hormone, exhibits numerous biological effects such as the antidiuretic effect, the pressor effect, and, in some tissues (e.g., the gastrointestinal tract), the vasoconstrictor effect. Furthermore, vasopressin shows to some extent residual activities of oxytocin, the other neurohypophyseal hormone, namely, the uterotonic and the lactation activity. The typical vasopressin-like activities may be therapeutically utilized in treatment of Diabetes insipldus, the general haermorrhage and haermorrhages of the gastrointestinal tract in particular. The application of the parent vasopressin is however accompanied by some unfavorable effects such as side reactions including the intestine and urinary bladder hypermotility and myocardial arrythmia as well s as very short-lived effect due to the enzymatic cleavage of the hormone.

Some known synthetic modifications of the vasopressin molecule wanted to remove at least partly the above drawbacks of the parent hormone and to limit the spectrum of biological activities. Thus, e.g., the slower enzymatic degradation of 1-deamino-8-D-argininevasopressin (DDAVP) may be ascribed to removal of the α-amino group of cysteine at position 1 and replacement of the natural amino acid at position 8 by its optical antipode. (Czechoslovak Patent No. 132,685) The DDAVP analog also exhibited a considerable disassociation vasopressin-like activities in favor of the antidiuretic activity. A completely different approach has been used in the case of the so called hormonogenes (Glypressin may be mentioned as a typical representative), i.e., synthetic analogs, the cysteine α-amino group at position 1 of which is acylated by an amino acid or by a short peptide chain (Czechoslovak Pat. No. 123,273). The stepwise removal of these additional amino acids in the organism leading to generation of the parent hormone, results in a prolonged (protracted) biological effect (Berankova-Ksandrova Z., Bisset G. W., Jost K., Krejci I, Pliska V., Rudinges J., Rychlik I., Sorm F.: Brit. J. Pharmacol 26 615 (1966)). Dangerous side effects are to a considerable extent eliminated since the level of the thus-liberated hormone in the organism is low. The drawback of the latter approach consists in a low specific activity (about one to two orders of magnitude lower when compared with the parent hormone) which requires application of a relatively high dose of the hormonogene.

All the above mentioned disadvantageous effects are circumvented by the present invention which relates to novel analogs of deamino-vasopressin with a modified disulfide bridge, according to the general formula I

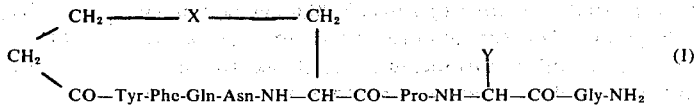

wherein X is a $-CH_2-S-$ or $-S-CH_2-$ fragment and Y is an aliphatic chain consisting of 2–5 carbon atoms, in which chain the α-carbon atom possesses the L or D configuration and the terminal ω-carbon atom carries a basic group such as an amino or guanidino group.

It has been observed that replacement of the disulfide bridge in the hormone by the $-CH_2-S-$ or $-S-CH_2-$ fragments considerably lowers the inactivation of the original vasopressin molecule; this modification does not lead to a decrease or elimination of biological activities (especially the antidiuretic activity and the haemodynamic activity) but results in their increase. Particularly valuable is the high antidiuretic activity and the vasoconstrictor effect on uterus. As shown by investigations in the field of oxytocin analogs, other replacements ($-CH_2-CH_2-$, $-CH_2-$, $-S-$, $-CH_2-S-CH_2-$) of the disulfide bridge result in a considerable decrease of biological activities (K. Jost, F. Sorm:Collect. Czech. Chem. Communs. 36, 234 (1971); K. Jost, F. Sorm:Collect. Czech. Chem. Communs. 36, 2975 (1971); Z. Prochazka, K. Jost, F. Sorm:Collect. Czech. Chem. Communs. 37, 289 (1972)). It is not surprising in this connection that the reported deamino-dicarba-analogs /$-S-S-$ replaced by $-CH_2-CH_2-$/ exhibit rather low biological activities (C. Hase, S. Shakibara, M. Wahrenburg, M. Kirchberger, I. L. Schwartz, R. Walter:J. Amer. Chem. Soc. 94, 3590 (1972)).

A further object of the present invention is to provide a manufacturing process of the novel analogs of deamino-vasopressin with a modified disulfide bridge, according to the general formula I. In this process, a linear peptide derivative according to the general formula II

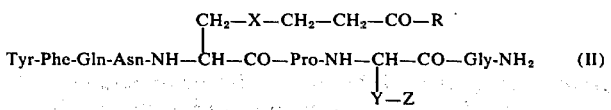

wherein R is a group activating the carboxylic function, Z is a protecting group for the amino or guanidino residue, and X as well as Y is the same as in the general formula I, is cyclized according to the method for the formation of the peptide bond, preferably according to the method of active esters, and the protecting group Z is removed in the last step by a known procedure, preferably by the action of liquid hydrogen fluoride or sodium in liquid ammonia.

The thus-prepared analogs according to the general formula I display a high antidiuretic activity: in the Burn test, their activity is 4–7 times higher than that of the parent hormone and the activity halftime is 50–10 times longer. The pressor effect (as determined by the blood pressure increase in rats) of analogs with a L-amino acid at position 8 is about one third lower than that of vasopressin itself while the values of the D-analogs are by 2 orders of magnitude lower. The uterotonic activity data (determined in vitro) exhibit a similar dependence.

The most remarkable results were obtained with the present analogs in investigations on the haemodynamic properties. Thus, the influence on the myocardial system, uterus and gastrointestinal tract, as well as the general peripheral vascular resistance were determined by means of the Sapirstein technique (determination of the blood flow as a function of the $^{86}$Rb content) (L. A. Saperstein:Circulation Research 4, 689 (1956)).

In view of the high specific activity and the long duration of action, the vasopressin analogs according to the general formula I may be used, in treatment of Diabetes insipidus and other diseases when the amount of urine should be lowered and when the haemorrhage from the gastrointestinal tract and uterus should be prevented, in cases accompanied by loss of blood, or, when a prolonged pharmacological activity on uterus is required.

The invention is illustrated by the following Examples which, however, are not to be taken as restrictive of the invention.

EXAMPLES

The intermediates in the preparation of compound II were obtained by a stepwise synthesis starting from the carboxylic end of the chain. In most cases, the α-amino group was protected by the o-nitrobenzenesulfenyl residue and the carboxylic function was activated by means of the active ester. For a survey of the intermediates see Table I (Example 1), Table II (Example 2), and Table III (Example 3). Melting points were taken on a heated microscope stage (Kofler block). Thin-layer chromatography was performed on silica gel in the following solvent systems:

SBA, 2-butanol — 25% aqueous ammonia — water (85 : 7.5 : 7.5);

SBN, 2-butanol — 90% aqueous formic acid — water (75 : 13.5 : 11.5); and

BAP, pyridine — 1-butanol — actic acid — water (10 : 15 : 3 : 6).

Paper electrophoresis was performed at 20 Volt/cm for 60 min in the 1M acetic acid (pH 2.4) and pyridine - acetate buffer (pH 5.7). Spots were detected with the use of ninhydrin; the ninhydrin-negative substances were detected by the chlorination method.

EXAMPLE 1

The following intermediates were prepared (all the amino acids are of the L-series):

a. tert-butyloxycarbonyl-ω-benzyloxycarbonylornithyl-glycine amide;

b. o-nitrobenzenesulfenylprolyl-ω-benzyloxycarbonylornithyl-glycine amide;

c. o-nitrobenzenesulfenylasparaginyl-S-β-methoxycarbonylethylhomocysteinyl-prolyl-ω-benzyloxycarbonylornithyl-glycine amide;

d. o-nitrobenzenesulfenylglutaminyl-asparaginyl-S-β-methoxycarbonylethylhomocysteinyl-prolyl-ω-benzyloxycarbonylornithyl-glycine amide;

e. o-nitrobenzenesulfenylphenylalanyl-glutaminyl-asparaginyl-S-β-methoxycarbonylethylhomocysteinyl-prolyl-ω-benzyloxycarbonylornithyl-glycine amide;

f. phenylalanyl-glutaminyl-asparaginyl-S-β-carboxyethyl-homocysteinyl-prolyl-ω-benzyloxycarbonylornithyl-glycine amide;

g. tert-butyloxycarbonyl-O-tert-butyltyrosyl-phenylalanyl-glutaminyl-asparaginyl-S-β-carboxyethylhomocysteinyl-prolyl-ω-benzyloxycarbonylornithyl-glycine amide;

h. o-nitrobenzenesulfenyl-O-tert-butyltyrosyl-phenylalanyl-glutaminyl-asparaginyl-S-β-carboxyethylhomocysteinyl-prolyl-ω-benzyloxycarbonylornithyl-glycine amide.

TABLE I

| Compound | Crystallized from | M.p. °C | $[α]_D$ (DMFA) | Yield, % | Analysis Calculated Found | | |
|---|---|---|---|---|---|---|---|
| | | | | | C | H | N |
| (a) | EtOAc | 125–127 | −2.2° | 72 | 56.90 | 7.16 | 13.27 |
| | | | | | 57.41 | 7.30 | 13.36 |
| (b) | MeOH-Et$_2$O | 152–155 | −30.0° | 76 | 54.60 | 5.63 | 14.68 |
| | | | | | 54.67 | 5.91 | 15.02 |
| (c) | MeOH-Et$_2$O | 137–140 | −54.4° | 62 | 50.75 | 5.83 | 14.02 |
| | | | | | 50.61 | 5.66 | 13.90 |
| (d) | MeOH-Et$_2$O | 161–165 | −40.0° | 76 | 49.85 | 5.93 | 14.88 |
| | | | | | 49.57 | 5.82 | 14.92 |
| (e) | DMFA-H$_2$O | 183–185 | −14.5° | 80 | 52.80 | 5.96 | 14.23 |
| | | | | | 52.63 | 5.76 | 14.47 |
| (f) | DMFA-Et$_2$O | amorphous | −34.0° | 67 | 51.85 | 6.58 | 14.78 |
| | | | | | 51.60 | 6.28 | 14.90 |
| (g) | DMFA-Et$_2$O | 192–194 | −33.0° | 81 | 56.60 | 6.79 | 12.59 |
| | | | | | 56.39 | 6.62 | 12.80 |
| (h) | DMFA-Et$_2$O | 180–183 | +13.7° | 90 | 55.35 | 6.17 | 13.13 |
| | | | | | 55.40 | 6.03 | 13.41 |

Abbreviations of solvents: DMFA, dimethylformamide; EtOAc, ethyl acetate; MeOH, methanol; Et$_2$O, diethyl ether. Water content of substances: (d), (e), (g), and (h), 1 molecule; (c), 0.5 molecule; (f) 2.5 molecule of water. Amino-acid analysis of compound (f): Gly 1.06, Orn 0.97, Pro 0.99, HCys (C$_2$H$_4$CO$_2$H) 0.98, Asp 1.03, Glu 1.00, Phe 0.99 (determined on an automatic analyzer after 20 hours of the hydrolysis with 6M HCl). Lactam of Tyrosyl-phenylalanyl-glutaminyl-asparaginyl-S-β-carboxyethylhomocysteinyl-prolyl-ω-benzyloxycarbonylornithyl-glycine Amide (i.e., Deamino[1]-carba[6]-ω-benzyloxycarbonyl-ornithine[8]-vasopressin)

To a solution of the protected octapeptide-acid (g) (400 mg) in a mixture of dimethylformamide (15 ml) and pyridine (15 ml) there is added with stirring and introduction of a stream of nitrogen bis-p-nitrophenyl sulfite (1.4 g). The whole is kept at room temperature for 7 hours, treated with additional reagent (1.4 g) and pyridine (7 ml), kept for 15 hours, and finally treated with 0.7 g of the reagent. Nitrogen is passed through the stirred mixture for additional 5 hours and the mixture is then evaporated to dryness. The residue is triturated with ether, the solid is collected with suction, washed thoroughly on the filter with ether and water, and air-dried. Yield, 405.7 mg (95%).

The active ester is dissolved in trifluoroacetic acid (8.0 ml), the solution kept at room temperature for 1 hour, diluted with toluene (10 ml), and evaporated to dryness. The residue is dissolved in dimethylformamide (15 ml) and the resulting solution is added at 50 °C in the atmosphere of nitrogen and with stirring to 400 ml of pyridine over 6 hours. The reaction mixture is kept at room temperature for 15 hours and then evaporated to dryness. The residue is triturated with ether, the solid is collected with suction, washed on the filter with ether, dried, and purified by counter-current distribution. The solid is dissolved in 25 ml of the upper phase of the solvent system 2 butanol - 0.05% aqueous acetic acid (1:1). The solution is added into the second tube and there are performed 184 transfers of the upper phase and 535 transfers of the lower phase. A peak with the distribution coefficient of 4.21 (tubes 22–67) is concentrated by evaporation and then freeze-dried to afford 180 mg (55%) of a product which is further purified for the purpose of analysis by gel filtration on Bio-gel in 3M acetic acid (180 mg of the product in 12 ml of 3M acetic acid was applied to a 140 × 2.5 cm column of Bio-gel P4; the flow rate was 12 ml per hour; the detection of the product was performed by absorption at 280 nm in 332–337 ml). The effluent is freeze-dried and reprecipitated from methanol with ether. The final yield was 112 mg (34%) of an analytically pure product. Optical rotation: $[\alpha]_D^{25}$ −52.4° (c 0.2; dimethylformamide). $R_F$ values: 0.33 (in SBA); 0.16 (in SBN); 0.67 (BAP). Amino acid analysis: Orn 0.98, Asp 1.05, Glu 1.01, Pro 0.98, Gly 1.02, Tyr 0.87, Phe 0.98, HCys ($C_2H_4CO_2H$) 1.13. For $C_{54}H_{71}N_{12}O_{14}S$. 4 $H_2O$ (1216.3) calculated: 53.30% C, 6.54%; H, 13.82%; N; found: 53.48% C, 5.93% H, 13.90% N.

Lactam of O-tert-Butyltyrosyl-phenylalanyl-glutaminyl-asparaginyl-S-β-carboxyethylhomocysteinyl-prolyl-ω-benzyloxycarbonyl-ornithyl-glycine Amide (i.e., Deamino[1]-carba[6]-O-tert-butyltyrosine[2]-ω-benzyloxycarbonylornithine[8]-vasopressin)

The acitve ester is prepared from the protected octapeptide-acid (h) (600 mg) analogously to the above mentioned process (20 ml of dimethylformamide, 30 ml of pyridine, 5 g of bis-p-nitrophenyl sulfite). Yield, 616.5 mg. (96%).

The active ester is dissolved in dimethylformamide (4 ml) and the solution is treated with 2M HCl in ether (0.5 ml) The reaction mixture is kept at room temperature for 5 min and then diluted with ether. The precipitate of the hydrochloride is collected with suction, washed on the filter with ether, dried in a desiccator over sodium hydroxide pellets, and finally dissolved in dimethylformamide (15 ml). The dimethylformamide solution is added over 6 hours to a mixture of pyridine (500 ml) and N-ethylpiperidine (54 μl) with stirring, heating to 50 °C is added over 6 hours to a mixture of pyridine (500 ml) and N-ethylpiperidine (54 μl) with stirring, heating to 50°C and in the atmosphere of nitrogen which is introduced into the mixture. The whole mixture is kept at room temperature for 15 hours and then evaporated to dryness. The residue is triturated with ether, collected with suction, washed on the filter with ether, and dried. The dry product is dissolved in 25 ml of the upper phase of the solvent system 2-butanol - 0.05% aqueous acetic acid (1:1) and subjected (vide supra) to the counter-current distribution (100 transfers of the upper phase). A peak with the distribution coefficient of 11.5 (tubes 81 to 102) is concentrated by evaporation and freeze-dried. Precipitation from methanol with ether affords 367 mg (73%) of a product, m.p. 159°–161°C, homogeneous on electrophoresis and chromatography. The analytical sample is purified by an analogous precipitation. Optical rotation: $[\alpha]_D^{25}$ −46.1° (c 0.2; dimethylformamide). $R_F$ values: 0.13 (in SBN); 0.72 (in BAP). For $C_{58}H_{78}N_{12}O_{14}S$ . 3 $H_2O$ (1253.4) calculated: 55.55% C, 6.75% H, 13.42% N; found: 55.39% C, 6.35% H, 13.48% N. Lactam of Tyrosyl-phenylalanyl-glutaminyl-asparaginyl-S-β-carboxyethylhomocysteinyl-prolyl-ornithyl-glycine Amide (i.e., Deamino[1]-carba[6]-ornithine[8]-vasopressin)

To a solution of the product described in the preceding paragraph (327 mg) in acetic acid (10 ml) there is added 35% hydrogen bromide in acetic acid (15 ml). The reaction mixture is heated to 50°C, kept at room temperature for 15 min, and diluted with ether. The precipitate of the hydrobromide is collected with suction, washed on the filter with ether, and dried in a desiccator over sodium hydroxide pellets. The hydrobromide is then dissolved in water (20 ml) and the aqueous solution is passed through a column of Amberlite IR-4B (OH[−] cycle) ion exchange resin (25 ml). The effluent is freeze-dried to afford 277 mg of a crude product which is purified by gel filtration on Bio-gel P4 in 1M acetic acid (55-mg portions of the product in 1.5 ml of 1M acetic acid were applied to a 100 × 1 cm column; flow rate, 7 ml per hour; the product was detected spectroscopically at 280 nm in the 66th to 76th ml; the by-product was in the 78th to 83rd ml). The effluent was freeze-dried to afford 128 mg (43%) of a product which was purified for analysis and biological assays by continuous free-flow electrophoresis and precipitated from methanolic solution with ether. Optical rotation: $[\alpha]_D^{25}$ −60.2° (c 0.24; 1M acetic acid). $E_{2.4}^{Gly}$ 0.66; $E_{5.7}^{His}$ 0.39. $R_F$ values: 0.09 (in SBA), 0.00 (in SBN), 0.43 (in BAP). Amino acid analysis: Asp 1.06, Glu 1.02, Pro 0.99, Gly 1.03, Tyr 0.92, Phe 0.99, Orn 0.93, HCys($C_2H_4CO_2H$) 1.05. For $C_{46}H_{64}N_{12}O_{12}S$ . $CH_3CO_2H$ . . 4 $H_2O$ (1141.1) calculated: 50.50% C, 6.71% H, 14.73% N; found: 50.48% C, 6.45% H, 15.03 N.

EXAMPLE 2

The following intermediates were obtained (all the amino acids are of the L-series):
a. benzyloxycarbonyl-S-β-methoxycarbonylethyl-homocysteinylprolyl-ω-tosylarginyl-glycine amide,
b. o-nitrobenzenesulfenylasparaginyl-S-β-methoxycarbonylethyl-homocysteinyl-prolyl-ω-tosylarginyl-glycine amide,
c. o-nitrobenzenesulfenylglutaminyl-asparaginyl-S-β-methoxycarbonylethylhomocysteinyl-prolyl-ω-tosylarginyl-glycine amide,
d. o-nitrobenezesulfenylphenylalanyl-glutaminyl-asparaginyl-S-β-methoxycarbonylethylhomocysteinyl-prolyl-ω-tosylarginyl-glycine amide,
e. phenylalanyl-glutaminyl-asparaginyl-S-β-carboxyethylhomocysteinyl-prolyl-ω-tosylarginyl-glycine amide, and
f. o-nitrobenezensulfenylfenyl-O-tert-butyltyrosyl-phenylalanyl-glutaminyl-asparaginyl-S-β-carboxyethylhomocysteinyl-prolyl-ω-tosylarginyl-glycine amide.

TABLE II

| Compound | Crystallized from | M.p. °C | $[\alpha]_D$ (DMFA) | Yield, % | Analysis Calculated Found | | |
|---|---|---|---|---|---|---|---|
| | | | | | C | H | N |
| (a) | iso-PrOH-Et$_2$O | 90–93 | −22.0° | 65 | 51.70 | 6.27 | 13.40 |
| | | | | | 51.69 | 6.34 | 13.70 |
| (b) | MeOH-Et$_2$O | 113–116 | −41.7° | 84 | 47.50 | 5.66 | 16.04 |
| | | | | | 47.31 | 5.54 | 15.74 |
| (c) | MeOH-Et$_2$O | 120–123 | −34.7° | 92 | 47.01 | 5.78 | 16.59 |
| | | | | | 46.91 | 5.73 | 16.34 |
| (d) | MeOH-Et$_2$O | 145–149 | −13.9° | 96 | 49.45 | 5.91 | 15.53 |
| | | | | | 49.45 | 5.75 | 15.76 |
| (e) | DMFA-MeOH-Et$_2$O | 148–153 | −26.9° | 86 | 49.24 | 6.34 | 16.62 |
| | | | | | 49.15 | 6.13 | 16.36 |
| (f) | DMFA-MeOH-Et$_2$O | 170–173 | +8.7° | 89 | 52.42 | 5.93 | 14.70 |
| | | | | | 52.62 | 6.07 | 14.40 |

Abbreviations of solvents: iso-PrOH, isopropyl alcohol; MeOH, methanol; DMFA, dimethylformamide; Et$_2$O, diethyl ether. Water content of substances: (b), 0.5 molecule; (a) and (c), 1 molecule; (f), 1.5 molecule; (d) and (e), 2 molecules of water. Amino acid analysis of substance (e): Arg 1.03, Asp 1.00, Glu 0.96, Pro 0.98, Gly 0.97, HCys c$_2$H$_4$CO$_2$H) 1.18, Phe P.93 (for the conditions see Table I). Lactam of O-tert-Butyl-tyrosyl-phenylalanyl-glutaminyl-asparaginyl-S-β-carboxyethylhomocysteinyl-prolyl-ω-tosylarginyl-glycine Amide (i.e., Deamino$^1$-carba$^6$-O-tert-butyltyrosine$^2$-ω-tosylarginine$^8$-vasopressin)

To a solution of the protected octapeptide-acid (f) (300 mg) in a mixture of dimethylformamide (10 ml) and pyridine (10 ml) there is added with stirring under nitrogen bis-p-nitrophenyl sulfite (1 g). The whole is kept at room temperature and treated with additional crops of the reagent (1 g, along with 5 ml of pyridine after 7 hours and then 0.5 g after 15 hours). The final reaction mixture is stirred at room temperature for 6 hours and evaporated to dryness. The residue is triturated with ether, collected with suction, washed on the filter with ether, dried, and precipitated from a methanolic solution with ether to afford 271 mg (83%) of a product.

To a solution of the above product in dimethylformamide (5 ml) there is added 2N hydrogen chloride in ether (0.2 ml), the reaction mixture kept at room temperature for 5 min, and precipitated with ether. The precipitate is collected with suction, washed thoroughly on the filter with ether, dried, and dissolved in dimethylformamide. The resulting solution is added over 4 hours into a mixture of pyridine (200 ml) and N-ethylpiperidine (25 μl) with stirring and heating to 50°C under nitrogen. The reaction mixture is kept at room temperature for 12 hours and evaporated to dryness. The residue is triturated with ether, collected with suction, washed on the filter with ether, and dried. The dry solid is dissolved in the upper phase (25 ml) of the solvent system 2-butanol - 0.05% aqueous acetic acid (1:1) and subjected to counter-current distribution (117 transfers of the upper phase and 175 transfers of the lower phase). A peak of the distribution coefficient 7.1 (tubes 60 to 103) is concentrated by evaporation and freeze-dried. Recrystallization from methanol-ether affords 58.6 mg (22%) of a product. R$_F$ values: 0.37 (in SBA); 0.23 (in SBN); and 0.78 (in BAP). Amino acid analysis: Arg 0.93, Asp 0.99, Glu 1.01, Pro 1.09, Gly 1.02, HCys (C$_2$H$_4$CO$_2$H) 0.96, Tyr 0.99, Phe 1.01.

Lactam of Tyrosyl-phenylalanyl-glutaminyl-asparaginyl-S-β-carboxyethylhomocysteinyl-prolyl-arginyl-glycine Amide (i.e. Deamino$^1$-carba$^6$-arginine$^8$-vasopressin)

The above protected cyclic octapeptide (56.0 mg) is reduced in anhydrous liquid hydrogen fluoride (10 ml) for 30 min. at 0°C. The hydrogen fluoride is evaporated in the vacuum of a water pump and the residue is dried for 2 hours under diminished pressure (oil pump). The dry solid is dissolved in 1M acetic acid (20 ml), the solution washed several times with ethyl acetate, the volatile components of the aqueous phase are removed by evaporation, and the residual liquid is freeze-dried. The product is dissolved in water (5 ml) and the aqueous solution is passed through a column of Amberlite IR-4B (acetate cycle; pH 2.5 ion exchange resin (1 ml). The effluent is freeze-dried and the residue is purified by gel filtration on Bio-gel P4 in 1M acetic acid and continuous free-flow electrophoresis to afford 22.3 mg (40%) of the product. R$_F$ values: 0.10 (in SBA); 0.00 (in SBN); and 0.51 (in BAP). E$_{2.4}^{Glu}$ 0.61, E$_{5.7}^{His}$ 0.36. Optical rotation:[α]$_D^{25}$ −62.0° (c 0.2; 1M acetic acid). For C$_{47}$H$_{66}$N$_{14}$O$_{12}$S . .CH$_3$CO$_2$H . 6 H$_2$O (1219.3) calculated: 48.30% C, 6.78% H, 16.10% N; found: 48.48% C, 6.25% H, 15.95% N. Amino acid analysis: Arg 1.03, Asp 1.05, Glu 1.01, Pro 0.94, Gly 1.00, HCys (C$_2$H$_4$CO$_2$H) 0.93, Phe 1.00, Tyr 1.00.

EXAMPLE 3

The following intermediates (arginine is of the D-series, all the remaining amino acids are of the L-configuration):

a. benzyloxycarbonyl-S-β-methoxycarbonylethyl-homocysteinyl-prolyl-ω-tosylarginyl-glycine amide, b. o-nitrobenzenesulfenylasparaginyl-S-β-methoxycarbonylethylhomocysteinyl-prolyl-ω-tosylarginyl-glycine amide, c. o-nitrobenzenesulfenylglutaminyl-asparaginyl-S-β-methoxycarbonylethylhomocysteinyl-prolyl-ω-tosylarginyl-glycine amide, d. o-nitrobenzenesulfenylphenylalanyl-glutaminyl-asparaginyl-S-β-methoxycarbonylethylhomocysteinyl-prolyl-ω-tosylarginyl-glycine amide, e. phenylalanyl-glutaminyl-asparaginyl-S-β-carboxyethylhomocysteinyl-prolyl-ω-tosylarginyl-glycine amide, and f. o-nitrobenzenesulfenyl-0.tert-butyltyrosyl-phenylalanyl-glutaminyl-asparaginyl-S-β-carboxyethylhomocysteinyl-prolyl-ω-tosylarginyl-glycine amide.

glycine Amide (i.e., Deamino[1]-carba[6]-D-arginine[8]-vasopressin).

TABLE III

| Compound | Crystallized from | M.p. °C | [α] (DMFA) | Yield % | Analysis Calculated, % Found, % | | |
|---|---|---|---|---|---|---|---|
| | | | | | C | H | N |
| (a) | iso-PrOH-Et₂O | 87–90 | −4.0° | 60 | 52.25 | 6.21 | 13.56 |
| | | | | | 52.23 | 6.44 | 13.25 |
| (b) | MeOH | 125–127 | −27.1° | 88 | 47.50 | 5.67 | 16.04 |
| | | | | | 47.68 | 5.72 | 15.57 |
| (c) | MeOH-Et₂O | 130–137 | −32.5° | 96 | 47.45 | 5.74 | 16.75 |
| | | | | | 47.62 | 5.90 | 16.30 |
| (d) | MeOH-Et₂O | 139–142 | +13.2° | 93 | 50.15 | 5.83 | 15.74 |
| | | | | | 50.15 | 5.76 | 15.73 |
| (e) | DMFA-MeOH-Et₂O | amorphous | −12.5° | 80 | 49.25 | 6.34 | 16.62 |
| | | | | | 49.25 | 6.04 | 16.51 |
| (f) | DMFA-MeOH-Et₂O | 174–177 | +21.0° | 88 | 52.62 | 6.07 | 14.40 |
| | | | | | 52.57 | 5.85 | 14.54 |

For the abbreviations of solvents see Table II. Water content of substances: (a), (b), and (c), 0.5 molecule; (d), 1 molecule; (f), 1.5 molecule; and (e), 2 molecules of water. Amino acid analysis, of substance (e): Gly 1.00, Arg 1.06, Pro 1.03, HCys ($C_2H_4CO_2H$) 1.20, Asp 1.07, Glu 0.94, Phe 0.91; substance (f): Gly 1.03, Arg 1.07, Pro 1.00, HCys ($C_2H_4CO_2H$) 1.01, Asp 1.07, Glu 0.97, Phe 0.98, Tyr 0.96. Lactam of O-tert-Butyltyrosyl-phenylalanyl-glutaminyl-asparaginyl-S-β-carboxyethylhomocysteinyl-prolyl-ω-tosyl-D-arginyl-glycine Amide (i.e., Deamino[1]-carba[6]-O.tert-butyltyrosine[2]-ω-tosyl-D-arginine[8]-vasopressin)

To a solution of the protected octapeptide-acid (f) (479 mg) in a mixture of dimethylformamide (15 ml) and pyridine (15 ml) there is added with stirring under nitrogen bis-p-nitrophenyl sulfite (1.5 g), the whole is stirred at room temperature for 8 hours, treated with another portion of the reagent (1.5 g) and pyridine (8 ml), stirred for additional 15 hours, and treated with 0.8 g of the reagent. After 6 hours, the reaction mixture is evaporated to dryness, the residue triturated with ether, collected with suction, washed on the filter with ether, dried, and reprecipitated from methanolic solution with ether. Yield, 440 mg (85%) of the product.

To a solution of this product in dimethylformamide (5 ml) there is added 2N hydrogen chloride in ether (0.4 ml), the mixture kept at room temperature for 5 min, and diluted with ether. The precipitate is collected with suction, washed on the filter with ether, dried, and dissolved in dimethylformamide. The resulting solution is added under nitrogen at 50° over 4 h to a mixture of pyridine (300 ml) and N-ethylpiperidine (40 μl) with stirring. The whole mixture is kept under nitrogen at room temperature for 12 hours and evaporated to dryness. The residue is triturated with ether, collected with suction, washed on the filter with ether, dried, dissolved in the upper phase (25 ml) of the solvent system 2-butanol - 0.05% aqueous acetic acid (1:1) and subjected to counter-current distribution (100 transfers of the upper phase). A peak of the distribution coefficient 12.5 (tubes 75-102) is concentrated and the concentrate freeze-dried. Recrystallization from methanol-ether affords then 199.3 mg (47%) of the product. $R_F$ values: 0.33 (in SBA); 0.20 (in SBN); and 0.67 (in BAP). Amino acid analysis: Arg 1.03, Asp 1.10, Glu 1.00, Pro 0.92, Gly 1.09, HCys ($C_2H_4CO_2H$) 0.98, Tyr 0.92, Phe 0.97.

Lactam of Tyrosyl-phenylalanyl-glutaminyl-asparaginyl-S-β-carboxyethylhomocysteinyl-prolyl-D-arginyl- The protected cyclic octapeptide (99.7 mg) from the preceding paragraph is reduced in anhydrous liquid hydrogen fluoride (10 ml) for 30 min at 0°C. The hydrogen fluoride is evaporated under diminished pressure (water pump). The residue is dried for 2 hours in vacuo (oil pump), dissolved in 1M acetic acid (30 ml), and the solution washed several times with ethyl acetate. The aqueous phase is evacuated and freeze-dried. The product of freeze-drying is dissolved in water (5 ml) and the aqueous solution is passed through a column of Amberlite IR-4B (acetate cycle; pH 2.5) ion exchange resin (1.5 ml). The effluent is freeze-dried and then purified by continuous free-flow electrophoresis and gel filtration on Bio-gel P4 in 1M acetic acid to afford 15.4 mg (19%) of the title substance. $R_F$ values: 0.13 (in SBA); 0.00 (in SBN); and 0.56 (in BAP). $E_{2.4}^{Glu}$ 0.66; $E_{5.7}^{His}$ 0.37. For $C_{47}H_{66}N_{14}O_{12}S \cdot CH_3CO_2H \cdot 7 H_2O$ (1237.3) calculated: 47.55% C, 6.85% H, 15.86% N; found: 47.72% C, 6.71% H, 15.69% N. Amino acid analysis: Gly 1.02, Arg 1.04, Pro 0.92, HCys ($C_2H_4CO_2H$) 0.80, Asp 1.06, Glu 1.00, Phe 1.00, Tyr 1.00.

We claim:

1. An analog of deamino-vasopressin having a modified disulfide bridge and having the formula

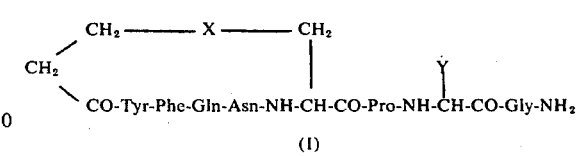

(I)

wherein X is —S—CH₂— and Y is an aliphatic group containing 2, 3 or 5 carbon atoms, in which group the α-carbon atom possesses L- or D-configuration and the terminal ω-carbon atom carries a member selected from the group consisting of amino and guanidino; and the hydroxy group on the tyrosine residue is optionally protected by a tert-butyl group.

2. An analog according to claim 1 designated as a lactam of O-tert-butyltyrosyl-phenylalanyl-glutaminyl-asparaginyl-S-β-carboxyethylhomocysteinyl-prolyl-ω-benzyloxycarbonyl-ornithyl-glycine amide.

3. An analog according to claim 1 designated as a lactam of tyrosyl-phenylalanyl-glutaminyl-asparaginyl-S-β-carboxyethylhomocysteinyl-prolyl-ornithyl-glycine amide.

* * * * *